Figure 1:
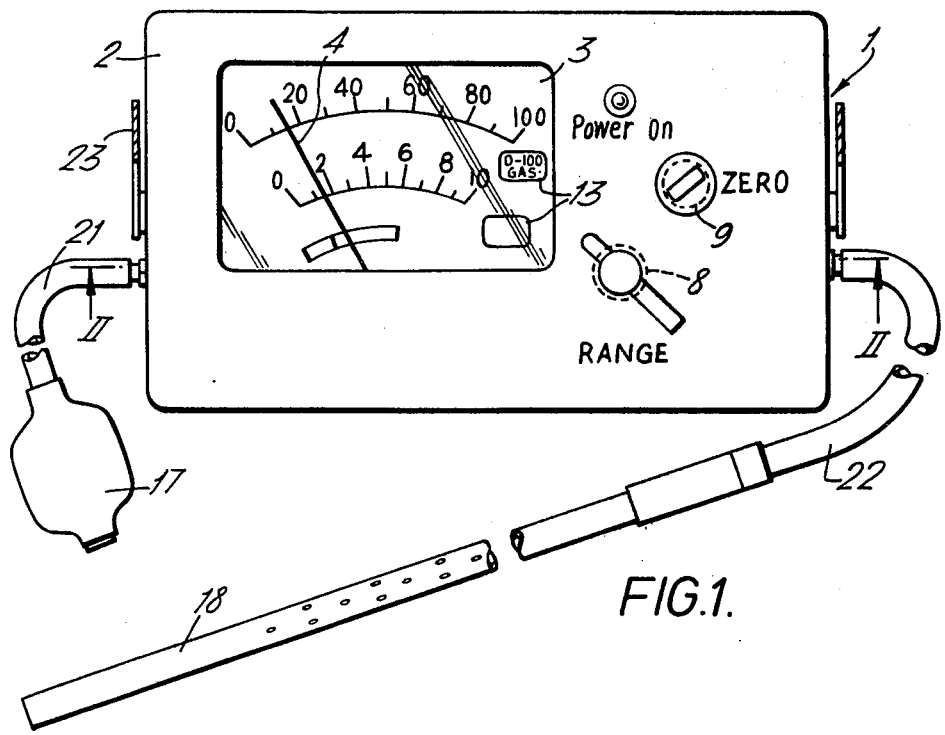

United States Patent [19]
Archbold et al.

[11] 4,173,886
[45] Nov. 13, 1979

[54] GAS DETECTORS

[75] Inventors: Thomas Archbold, Whitley Bay; Michael R. G. Sharp, Seaton Sluice, both of England

[73] Assignee: British Gas Corporation, London, England

[21] Appl. No.: 919,564

[22] Filed: Jun. 27, 1978

[51] Int. Cl.² .......................................... G01N 31/00
[52] U.S. Cl. .................................. 73/23; 73/421.5 R
[58] Field of Search ............. 73/23, 421.5 R; 422/83, 422/88, 94, 98; 340/632

[56] References Cited
U.S. PATENT DOCUMENTS 2,162,395  6/1939  Bennett .................................. 422/83
3,956,940  5/1976  Guild ............................. 73/421.5 R
3,973,848  8/1976  Jowett et al. ............................. 73/23

FOREIGN PATENT DOCUMENTS
1447488  8/1976  United Kingdom ....................... 73/23

Primary Examiner—Stephen A. Kreitman
Attorney, Agent, or Firm—Larson, Taylor and Hinds

[57] ABSTRACT

This invention relates to portable gas detectors having means for aspirating a sample of the atmosphere to be tested into the vicinity of two sensor devices, and including a water-trap comprising valve means arranged, in response to a drop in pressure in the flow line when water is accidentally sucked in with an aspirated sample, to temporarily close the sample flow path or to open a by-pass for detecting the presence of both natural gas and manufactured gas in the atmosphere.

9 Claims, 5 Drawing Figures

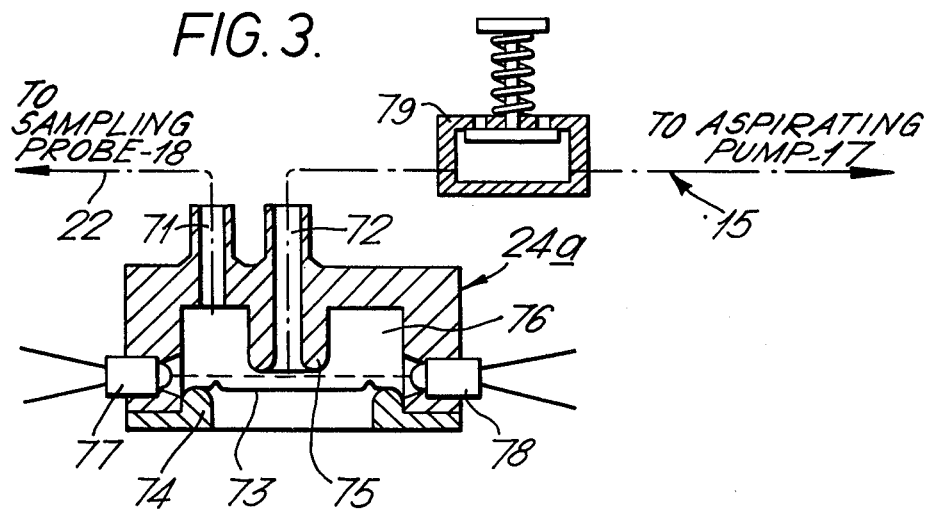
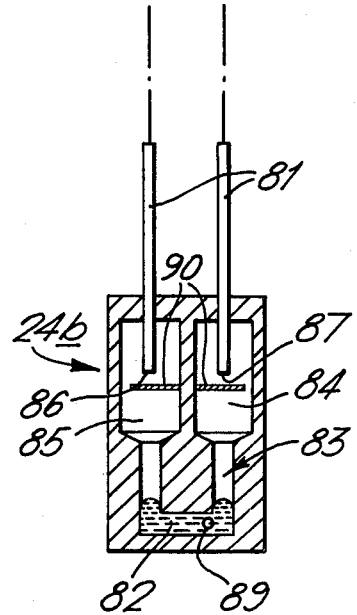
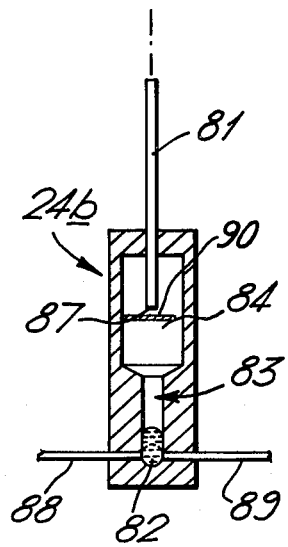

GAS DETECTORS

This invention relates to portable gas detectors, and particularly, although not exclusively, to instruments capable of detecting the presence of both natural gas and manufactured gas in atmosphere.

In British Patent Specification No. B.1,447,488 there is described and claimed a portable gas detector for sensing the presence of gas in an aspirated sample of the atmosphere to be tested, and for giving an indication of the level of gas concentration in the sample.

Said British Patent Specification also describes and claims such a portable gas detector incorporating a water-trap and a filter unit arranged in the flow path of the aspirated atmospheric sample.

It has been found in use of such detectors that the examples of water-trap and filter described in said British Patent Specification frequently allow ground water inadvertently to be drawn into the instrument with the aspirated sample, particularly during bore hole measurements when an operator is not aware that water is present at the bottom of the bar hole. Such induction of water into the instrument can damage its gas sensing means and render it temporarily useless until costly repairs have been carried out.

Even where, in such an instrument, the water-trap is of the capillary type comprising a cylindrical cotton filter fitted into the flow line of the instrument, this is not always satisfactory since the pumping force of the aspirator bulb is greater than the surface tension forces in the wet water trap filter.

More recently, gas detectors have been provided with a form of water knock-out pot in the flowpath between the instrument sample-inlet nipple and gas sensor devices. This arrangement has the disadvantage that usually the pot is fitted downstream from a cotton filter, which must be replaced as in other instruments; in addition, the pot capacity is usually too small to provide adequate protection if the filter is incorrectly fitted. Furthermore, whilst in some cases the pot will hold all the water accidentally present in an aspirated sample pumped by one stroke of an aspirator bulb, repeated operation of the bulb can cause water to be drawn into the instrument.

Other known instruments use a simple valve at its probe inlet connection, which valve is usually actuated by a movable float upon entry of water into its float chamber. Such valves are usually bulky and are sensitive to dirt present in the water which prevents closure of the valve.

An object of the present invention is to provide an improved portable gas detector which is less subject to the aforesaid disadvantages.

According to the present invention in a portable gas detector having means for aspirating a sample of the atmosphere to be tested through a flowline in the detector into the vicinity of its gas-sensing means, and having a water-trap associated with said flowline, the water trap comprises valve means arranged, in response to a drop in pressure which occurs in said flow line through the instrument when water is accidentally sucked into the probe with an aspirated sample, to interrupt the flow of said water-containing sample through the flow line of the instrument.

It will be appreciated that the invention makes use of the presence of a partial vacuum in the flow line produced by the action of accidentally 'lifting' a quantity of water into the instrument probe tube when the aspirator bulb is operated to test for gas with the remote end of the probe submerged in water.

Typically, when the aspirator bulb of a gas detector is operated and pumps a sample of the atmosphere only, almost all of the pressure differential generated by the bulb will be dissipated between the inlet and the outlet ports of the instrument. Measurements made during trials show that the pressure loss between the probe inlet and the instrument is about 0.6 inch water gauge. If water accidentally enters the probe during the pumping action, the air flow rate through the instrument is reduced and a significant pressure loss develops between the surrounding air and the instrument inlet port. Depressions of 6–25 ins. water gauge have been measured as the operation of the aspirator bulb begins to pull or lift water into the probe.

Various methods of interrupting the flow of a water-containing sample in the flow line may be employed, for example, a spring-loaded shut-off valve triggered by a pressure sensitive diaphragm set, at say 12 inch water gauge. Such a valve would require to be reset after the probe had been cleared of water or other blockage. Alternatively, a thin walled tube capable of collapsing so as to seal the sample tube at pressure reductions greater than for example 12 ins. water gauge may be used.

Preferably however, the valve means according to one aspect of the invention for interrupting the flow of a water-containing sample through the flow line may consist of a flexible diaphragm valve connected in the flow line, for example in the sample flow line upstream of the instrument flow path, the flexible diaphragm of the valve being normally spaced from the valve seating to permit through flow of an aspirated sample but arranged to move so as to seal against the valve seating upon said pressure drop occurring, for example of the order of 12 ins. water gauge, so as to close the flow line.

Once the diaphragm valve has closed, the trapped subatmospheric pressure in the flow line of the instrument will hold it closed. A manually operable pressure relief valve can be fitted in the flow line which, when operated, allows the diaphragm valve to relax and open.

Alternatively, the valve means according to another aspect to the invention for interrupting the flow of a water-containing sample through the flow line may comprise a branch pipe connecting the flow line to atmosphere through a liquid manometer valve whose liquid (e.g. mercury) will normally seal off the branch pipe but will be moved into an enlarged portion of the valve passageway upon said pressure drop occurring. The quantity and nature of manometer fluid will depend on the pressure differential at which the by-pass will open to atmosphere.

Each end of the manometer passageway containing the liquid terminates in an enlarged chamber into which a respective open end of the by-pass branch pipe communicates. The capacity of each chamber should be sufficient to hold all of the manometer liquid without obstructing the open ends of the by-pass pipe, irrespective of the orientation of the manometer.

When pumping gas/air mixtures only, the manometer valve will register the small pressure loss up to the branch connection, but the branch will remain sealed by the manometer fluid. If water enters the probe, resulting in an increase in the pressure loss beyond a predetermined value, (say 12 ins. water gauge) the manometer liquid will be blown into the chamber nearest the sample line allowing air to flow through the manometer passageway into the sample line, thereby preventing any further flow from the probe to the instrument.

Preferably, both chambers should contain a baffle plate to prevent the liquid being carried into the connecting pipes. In normal use, the manometer would be mounted upright in the gas detector case. The manometer liquid will automatically run back into the passageway sealing the by-pass as soon as the differential pressure in the flow line is reduced to acceptable values.

Whatever protective device is employed in the gas detector, the action of the detector will provide misleading indications on its indicator panel when the valve means is in action. Consequently, it will be desirable to provide means for giving an indication that the valve means is in action so as to warn a user of the instrument of such misleading indications.

For example, in the case of valve devices which close the sample line, the closing of the valve could switch an electronic circuit to activate a warning light, such as a flashing light emitting doide mounted in a conspicuous position on the instrument panel. Similarly, the presence of manometer liquid in the low pressure chamber of the manometer device (or the absence of liquid from the manometer) could be sensed using electrical contacts set into the manometer wall, or capacitive plates mounted on the manometer itself.

Figure 2:
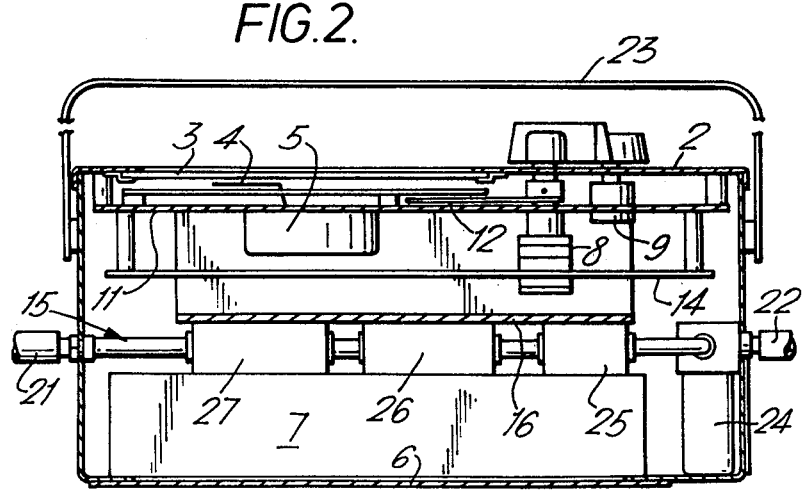

Two embodiments of a valve means for use in a portable gas detector in accordance with the present invention are shown by way of example in the accompanying drawings in which FIG. 1 is a plan view of the detector, FIG. 2 is a sectional side elevation on the line II—II of FIG. 1, FIG. 3 is a diagrammatic sectional view of a diaphragm valve of one embodiment for closing the sample probe line of the detector, and incorporating a pressure relief valve for releasing any developed partial vacuum in the flow line, and FIGS. 4 and 5 are diagrammatic sectional views at right angles to each other of a liquid manometer by-pass valve of the second embodiment.

Referring first to FIGS. 1 and 2, the portable detector unit comprises a metal container for the instrumentation having a box body 1 whose open top is closed by a detachably secured cover plate 2 which is provided with a window panel 3 for enabling an operator to obtain a gas concentration reading from the deflection of the pointer 4 of an indicating ammeter 5 against a suitably calibrated scale plate. The base of the box 1 is provided with a detachable cover plate 6 giving access to a compartment in which electric power supply batteries 7 are located. The component parts of the metal container are preferably coated with plastics material. A multi-way "off/battery check/range" selector switch 8 and a pointer zero-setting control 9, together with the meter 5, are suitably mounted on a spine member 11 carried by the cover plate 2. Attached to the spindle of the selector switch 8 is a flag disc 12 which carries legends representative of particular detection range or battery check position for the switch, and which legends are selectively displayed through apertures 13 in the scale plate. A printed circuit board 14 carrying some of the electrical components (not shown) of a circuit arrangement and a flow line system (indicated generally at 15) for the aspirated sample of atmosphere to be tested, is supported within the container by any suitable means, possibly from the spine member 11 by suitable mounting means shown schematically at 16. A rubber aspirator bulb 17 and a sample probe 18 are connected, in use of the instrument, to the respective ends of the flow system 15 by detachable flexible tubes 21 and 22 respectively.

The flexible hose 22, which is about 2 meters long, is preferably of a material which does not absorb any component of the gases being detected, and the sample probe 18 is, e.g., constructed as a 0.5 m. length of 5 mm. inside diameter tube sealed at its outermost end and provided with a plurality of radial holes 10–15 cm. from the sealed end. The probe tube is formed of a suitable material which will not produce sparks in use. Preferably, the aspirator bulb 17 is designed such that it can only be connected to the instrument in the correct manner, i.e. it cannot be interchanged with the sample tube.

The instrument container can be provided with a carrying handle 23 (only part of which is shown) and may be enclosed in a padded leather carrying jacket (not shown) provided with appropriate apertures for viewing the meter scale and for access to the knobs of the selector switch and zero control 8 and 9 respectively.

Generally, the flow system through which the aspirated sample is caused to flow from the probe 18, consists of a series connected water-trap 24, a filter unit 25, a thermal conductivity sensor device 26 for detection of from 0% to 100% of gas in air, and a catalytic sensor device 27 for detection of from 0% to 100% of the lower explosive limit of gas in air (L.E.L.) and also from 0% to 10% (L.E.L.)

Referring also to FIG. 3 of the accompanying drawings, the inlet and outlet ports 71, 72 of a water-trap diaphragm valve 24a of the first embodiment are connected in the flow system 15 (represented herein as a chain-dotted line) and preferably upstream of the instrument filter unit 25 in the sample probe line 22. A flexible diaphragm 73 is mounted, by means of a clamping ring 74, across a valve seating 75 and forms a closure for a compartment 76 communicating the sampling probe 18 and aspirator bulb or pump 17. The diaphragm 73 is normally spaced from the valve seating 75 (as shown) to permit free flow of an aspirated sample but is arranged to flex against the valve seating 75 and close the port 72 upon a pressure drop occurring in the chamber 76.

The flexing of the diaphragm 73 against the valve seating is used to interrupt a beam of light from a light source 77 directed onto a light detector diode 78 which can be arranged to initiate an output signal for producing a warning indication on the instrument panel of the presence of water in the sampling probe in well known manner.

A simple manually-operated pressure relief valve 79 may be connected in series with the diaphragm valve 24a for releasing the partial vacuum in the chamber 76 and therefore relaxing the flexible diaphragm from its valve seating.

Referring now to FIGS. 4 and 5, a valve means of the second embodiment for opening a normally closed branch line to the flow line 15 consists of a liquid mercury manometer valve 24b connected in a pipe 81 which is a branch line from the sampling probe line 22 to atmosphere. The valve is fitted in the instrument in the upright position (as shown) so that a quantity of mercury 82 normally rests in the relatively narrower base part of a U-shaped passageway 83 but, when water is being 'lifted' in the sampling line 22 and thereby creating a partial vacuum in an enlarged portion 84 of the passageway 83, the mercury will be 'sucked' into the enlarged portion 84 thereby to vent the sampling line to atmosphere. A further enlarged portion 85 of the passageway 83 is provided, the capacities of which enlarged portions 84, 85 being sufficient to hold all of the mercury without obstructing the open ends 86, 87 of the branch pipe 81 projecting into the respective enlarged portions. The enlarged portions 84 and 85 are provided with a baffle plate 90.

Electric current carrying conductors 88, 89 are sealed through the walls of the valve body (which will be of insulating material) to form contacts of an electric circuit arrangement (not shown) which is completed by the presence of the mercury and broken under a partial vacuum condition when the mercury evacuates the region between the contacts. This interruption of the electrical circuit provides a simple signal means for initiating a warning indication, in well known manner, to an operator of the presence of water in the sampling tube.

Either valve can conveniently be constructed in a compact form so as to fit easily into the casing of the present form of gas detector referred to and illustrated in our copending Patent Application and not need frequent replacement.

We claim:

1. A portable gas detector having means for aspirating a sample of the atmosphere to be tested through a flow line in the detector into the vicinity of its gas-sensing means, and having a water-trap associated with said flow line, wherein said water trap comprises valve means arranged, in response to a drop in pressure which occurs in the flow line through the instrument when water is accidentally sucked into the probe with an aspirated sample, to interrupt the flow of said water-containing sample through the flow line of the instrument.

2. A portable gas detector according to claim 1, wherein said valve means for interrupting the flow of a water-containing sample through the flow line consists of a flexible diaphragm valve connected in the flow line, the flexible diaphragm of the valve being normally spaced from the valve seating to permit through flow of an aspirated sample but arranged to move so as to seal against the valve seating upon said pressure drop occurring so as to close the flow line.

3. A portable gas detector according to claim 2, wherein the diaphragm valve is connected in the flow line upstream of the instrument.

4. A portable gas detector according to claim 2 or claim 3, including a manually operable pressure relief valve fitted in the flow line arranged upon manual operation of the relief valve to allow the flexible diaphragm to relax and open the diaphragm valve.

5. A portable gas detector according to claim 1, wherein the valve means for interrupting the flow of a water-containing sample through the flow line consists of a branch pipe connecting the flow line to atmosphere through a liquid manometer valve whose liquid normally seals off the branch pipe from atmosphere but will be moved into an enlarged portion of the manometer valve passageway upon said pressure drop occurring so as to vent said flow line to atmosphere.

6. A portable gas detector according to claim 5, wherein the branch pipe and its associated manometer is connected in the flow line upstream of the instrument, and each end of the manometer passageway containing said liquid terminates in an enlarged chamber into which a respective open end of the branch pipe communicates, the capacity of each chamber being sufficient to hold all of the manometer liquid without obstructing the open ends of the branch pipe.

7. A portable gas detector according to claim 6, wherein both chambers contain a baffle plate for preventing the liquid being carried into said open ends of the branch pipe.

8. A portable gas detector according to claim 5 or 6 or 7, wherein the manometer valve is mounted upright in the gas detector casing such that the manometer liquid will automatically run back into said manometer passageway sealing the branch pipe as soon as differential pressure in the flow lines is reduced to acceptable values.

9. A portable gas detector according to claim 1 or 2 or 3 or 5 or 6 or 7, including means for giving an indication on an indicating panel of the detector when said valve means is in action.

* * * * *